United States Patent [19]
Reichert et al.

[11] Patent Number: 5,814,565
[45] Date of Patent: Sep. 29, 1998

[54] INTEGRATED OPTIC WAVEGUIDE IMMUNOSENSOR

[75] Inventors: W. Monty Reichert, Durham, N.C.; James N. Herron, Salt Lake City, Utah; Douglas A. Christensen, Salt Lake City, Utah; Hsu-Kun Wang, Salt Lake City, Utah

[73] Assignee: University of Utah Research Foundation, Salt Lake City, Utah

[21] Appl. No.: 393,450

[22] Filed: Feb. 23, 1995

[51] Int. Cl.⁶ ........................... G01N 33/53; G01N 21/17
[52] U.S. Cl. ................................... 422/82.11; 422/82.05; 436/525; 385/12
[58] Field of Search ............................ 422/82.05–82.11; 436/525; 385/12

[56] References Cited

U.S. PATENT DOCUMENTS

| Re. 33,064 | 9/1989 | Carter et al. |
|---|---|---|
| Re. 34,394 | 9/1993 | Bunting ................................. 436/500 |
| 3,934,061 | 1/1976 | Keck et al. |

(List continued on next page.)

FOREIGN PATENT DOCUMENTS

| 2220083 | 12/1989 | United Kingdom . |
|---|---|---|
| 9001166 | 2/1990 | WIPO . |
| 9113339 | 9/1991 | WIPO . |

OTHER PUBLICATIONS

Harrick et al., "Multiple Internal Reflection Fluorescence Spectrometry", Analytical Chemistry, vol. 45, No. 4, pp. 687–689, 691, Apr. 1973.

Ives et al., "Protein Adsorption on the Surface of a Thin–Film Polymer Integrated Optical Waveguide", Applied Spectroscopy, vol. 42, No. 1, pp. 68–72, 1988.

Ives et al., "Total Internal Reflection Fluorescence Surface Sensors.", Optical Fiber Sensors, pp. 391–396, 1987.

Pecht et al., "Kinetics of Antibody–Hapten Interactions", Molecular Biology, Biochem. and Biophysics, pp. 308–309, 311, 313, 315, 317, 319, 321, 323–324, 326, 328, 330, 332, 334, 336, 338, 1977.

Walker et al., "Integrated Optical Waveguide Attenuated Total Reflection Spectrometry and Resonance Raman Spectroscopy of Adsorbed Cytochrome c", J. Phys. Chem., vol. 97, No. 39, pp. 10217–10222, 1993.

Walker et al., "Corning 7059, Silicon Oxynitride, and Silicon Dioxide Thin–Film Integrated Optical Waveguides: In Search of Low Loss, Nonfluorescent, Reusable Glass Waveguides", Applied Spectroscopy, vol. 46, No. 9, pp. 1437–1441, 1992.

(List continued on next page.)

*Primary Examiner*—Lyle A. Alexander
*Attorney, Agent, or Firm*—Trask, Britt & Rossa

[57] ABSTRACT

A step-gradient composite waveguide for evanescent sensing in fluorescent binding assays comprises a thick substrate layer having one or more thin film waveguide channels deposited thereon. In one embodiment, the substrate is silicon dioxide and the thin film is silicon oxynitride. Specific binding molecules having the property of binding with specificity to an analyte are immobilized on the surface of the thin film channels. In preferred embodiments, the composite waveguide further includes light input coupling means integrally adapted to the thin film channels. Such light coupling means can be a grating etched into the substrate prior to deposition of the thin film, or a waveguide coupler affixed to the upper surface of the thin film. The waveguide coupler has a thick input waveguide of high refractive index which receives the laser light through one end and propagates it by total internal reflection. The propagated light is then coupled evanescently into the thin film waveguide across a spacer layer of precise thickness and having an index of refraction lower than either the input waveguide or the thin-film waveguide. The composite waveguide can be constructed by plasma vapor deposition of silicon oxynitride onto the silicon dioxide substrate, masking the channel waveguides with a photoresist, and using reactive ion etching to expose the substrate in the unmasked regions.

21 Claims, 5 Drawing Sheets

U.S. PATENT DOCUMENTS

| | | |
|---|---|---|
| 3,939,350 | 2/1976 | Kronick et al. . |
| 4,166,105 | 8/1979 | Hirschfeld . |
| 4,264,766 | 4/1981 | Fischer ................................ 536/51 |
| 4,298,685 | 11/1981 | Parikh et al. . |
| 4,450,231 | 5/1984 | Ozkan . |
| 4,857,273 | 8/1989 | Stewart . |
| 4,866,681 | 9/1989 | Fertig . |
| 4,880,752 | 11/1989 | Keck et al. ...................... 422/82.11 |
| 4,892,383 | 1/1990 | Klainer et al. . |
| 4,893,894 | 1/1990 | Caimi . |
| 4,909,990 | 3/1990 | Block et al. . |
| 4,913,519 | 4/1990 | Klainer et al. . |
| 4,940,328 | 7/1990 | Hartman . |
| 4,945,245 | 7/1990 | Levin . |
| 5,000,540 | 3/1991 | Nakamura . |
| 5,006,333 | 4/1991 | Seifer et al. ........................... 424/78 |
| 5,006,716 | 4/1991 | Hall . |
| 5,043,278 | 8/1991 | Nagaoka et al. ................... 435/181 |
| 5,059,396 | 10/1991 | Opitz et al. . |
| 5,064,619 | 11/1991 | Finlan . |
| 5,081,012 | 1/1992 | Flanagan et al. . |
| 5,132,095 | 7/1992 | Koshiishi et al. . |
| 5,156,972 | 10/1992 | Issachar . |
| 5,156,976 | 10/1992 | Slovack et al. . |
| 5,164,589 | 11/1992 | Sjodin . |
| 5,166,515 | 11/1992 | Attridge . |
| 5,173,747 | 12/1992 | Boiarski et al. . |
| 5,192,502 | 3/1993 | Attridge et al. . |
| 5,192,510 | 3/1993 | Zoha et al. . |
| 5,202,230 | 4/1993 | Kamentsky . |
| 5,212,099 | 5/1993 | Marcus . |
| 5,221,958 | 6/1993 | Bohnenkamp . |
| 5,224,188 | 6/1993 | Vali . |
| 5,248,620 | 9/1993 | Sluka et al. ......................... 436/531 |
| 5,249,251 | 9/1993 | Egalon et al. . |
| 5,262,638 | 11/1993 | Egalon et al. . |
| 5,266,486 | 11/1993 | Fraatz et al. . |
| 5,268,305 | 12/1993 | Ribi et al. . |
| 5,274,721 | 12/1993 | Dickinson et al. . |
| 5,300,423 | 4/1994 | Zoha et al. . |
| 5,327,225 | 7/1994 | Bender et al. . |
| 5,340,715 | 8/1994 | Slovacek et al. . |
| 5,340,722 | 8/1994 | Wolfbeis et al. . |
| 5,343,550 | 8/1994 | Egalone et al. . |
| 5,344,784 | 9/1994 | Attridge ............................... 436/158 |
| 5,354,574 | 10/1994 | Kobayashi et al. . |
| 5,372,936 | 12/1994 | Fraatz et al. . |
| 5,377,008 | 12/1994 | Ridgway et al. . |
| 5,399,866 | 3/1995 | Feldman et al. . |
| 5,401,469 | 3/1995 | Kobayashi et al. . |
| 5,413,939 | 5/1995 | Gustafson et al. . |
| 5,416,579 | 5/1995 | Barshad et al. . |
| 5,422,283 | 6/1995 | Ismail . |
| 5,426,032 | 6/1995 | Phillips et al. . |
| 5,427,915 | 6/1995 | Ribi et al. . |
| 5,432,096 | 7/1995 | Zhu . |
| 5,437,840 | 8/1995 | King et al. . |
| 5,449,625 | 9/1995 | Kobayashi et al. . |
| 5,478,755 | 12/1995 | Attridge et al. . |
| 5,492,674 | 2/1996 | Meserol . |
| 5,494,798 | 2/1996 | Gerdt et al. . |
| 5,494,803 | 2/1996 | Carbonell et al. . |
| 5,514,596 | 5/1996 | King et al. . |
| 5,538,850 | 7/1996 | King et al. . |
| 5,552,272 | 9/1996 | Bogart . |

OTHER PUBLICATIONS

R. Wurmser, "Thermodynamic study of antigen–antibody reactions", Experimental Methods in Biophysical Chemistry, pp. 613–647.

Lee, Jin Ho; Kopecek, J. and Andrade, J.D., "Protein–resistant surfaces prepared by PEO–containing block copolymer surfactants", Journal of Biomedical Materials Research, Published by John Wiley & Sons, pp. 351–368 (1989).

Carlsson, J.; Drevin, K. and Axen, R., Protein Thiolation and Reversible Protein–Protein Conjugation, Biochem J. (1978) 173, 723–737, Printed in Great Britain.

ND OPTIC WAVEGUIDE
IMMUNOSENSOR

LICENSE RIGHTS

The research supporting this invention was partially funded by National Institute of Health Grant #HL32132. The United States Government may have some rights in this invention.

BACKGROUND OF THE INVENTION

1. Field of the Invention

The invention relates to apparatus for solid-state biochemical binding assays, and especially to optical structures utilizing evanescent sensing principles for use in such apparatus and assays.

2. State of the Art

Immunoassays exploiting the properties of an optical technique known as total internal reflection (abbreviated TIR) are proving to be a valuable tool for detection of analytes at concentrations of $10^{-10}$ to $10^{-13}$ molar or below, without a wash step. When a light beam traveling in a waveguide is totally internally reflected at the interface between the waveguide and an adjacent medium having a lower refractive index, a portion of the electromagnetic field of the TIR light penetrates shallowly into the adjacent medium. This phenomenon is termed an "evanescent penetration" or "evanescent light". The intensity of evanescent light drops off exponentially with distance from the waveguide surface.

Binding assays in general are based on the strong affinity of a selected "capture" molecule to specifically bind a desired analyte. The capture molecule/analyte pair can be an antibody/antigen pair or its converse, a receptor/ligand pair or its converse, etc. as known in the art. In a fluorescent binding assay, the binding of the analyte to the antibody is monitored by a tracer molecule which emits fluorescent light in response to excitation by an input light beam.

One of several possible schemes for exploiting the properties of evanescent light fields for fluorescence measurements is as follows. If an antibody is immobilized on an optical structure in which a light beam is being propagated by TIR, the resulting evanescent light can be used to selectively excite tracer molecules that are bound (whether directly or indirectly) to the immobilized antibody. Tracer molecules free in solution beyond the evanescent penetration depth are not excited, and therefore do not emit fluorescence. For silica-based optical materials or optical plastics such as polystyrene, with the adjacent medium being an aqueous solution, the evanescent penetration depth is generally about 1000 to 2000 Å (angstroms). The amount of fluorescence is thus a measure of the amount of tracer bound to the immobilized capture molecules. The amount of bound tracer in turn depends on the amount of analyte present, in a manner determined by the specifics of the inmunoassay procedure.

U.S. Pat. No. RE 33,064 to Carter, U.S. Pat. No. 5,081, 012 to Flanagan et al, U.S. Pat. No. 4,880,752 to Keck, U.S. Pat. No. 5,166,515 to Attridge, and U.S. Pat. No. 5,156,976 to Slovacek and Love, and EP publications Nos. 0 517 516 and 0 519 623, both by Slovacek et al, all disclose apparatus for immunoassays utilizing evanescent sensing principles.

Desirably, an immunosensor should be capable of accurately and repeatably detecting analyte molecules at concentrations of $10^{-13}$M (molar) to $10^{-15}$M and preferably below. At present, such sensitivity is not believed to be available in a commercially practical and affordable immunosensor. Also desirably, an immunosensor should provide multiple "channels", that is, the capacity for measuring multiple analytes and multiple measurements of the same analyte, on the same waveguide substrate. Such an immunosensor would allow both self-calibration with known standards, and screening for a panel of different analytes selected for a particular differential diagnostic procedure.

One approach to improving the sensitivity (lowering the detection limits) of fluorescent immunosensors, proposed by Ives et al. (Ives, J. T.; Reichert, W. M.; Lin, J. N.; Hlady, V.; Reinecke, D.; Suci, P. A.; Van Wagenen, R. A.; Newby, K.; Herron, J.; Dryden, P. and Andrade, J. D. "Total Internal Reflection Fluorescence Surface Sensors" in A. N. Chester, S. Martellucci and A. M. Verga Scheggi Eds. *Optical Fiber Sensors*, NATO ASI Series E, Vol 132, 391–397, 1987), is to use waveguides which are very thin, perhaps about 1 m in thickness. Such thin waveguides may provide higher evanescent intensity and a reflection density of 500–1000 reflections/cm or more. However, the potential lowering of the detection limit by use of thin-film waveguides is achievable only if the waveguide material is nonfluorescent and low-loss. Most present evanescent immunosensing technology ("thick" waveguides) utilizes silica glass ($SiO_2$), which is intrinsically nonfluorescent. Only the purest grades of silica, for example UV grade quartz which is rather expensive, lack the additives and impurities that fluoresce Dierker, et al., 1987).

Further, one cannot simply fabricate silica-on-silica waveguides by depositing $SiO_2$ onto a quartz substrate because there would be no refractive index difference. Instead one must either (1) fabricate a glass waveguide of higher refractive index than the underlying silica substrate, or (2) deposit a silica waveguide onto a transparent substrate of a lower refractive index. Therefore, other materials must be employed.

Thin film waveguides have been described by Sloper et al. ("A planar indium phosphate monomode waveguide evanescent field immunosensor", *Sensors and Actuators* B1:589–591, 1990) and Zhou et al. ("An evanescent fluorescence biosensor using ion-exchanged buried waveguides and the enhancement of peak fluorescence", *Biosensors and Bioelectronics* 6:595–607, 1991. However, neither of these devices was capable of achieving detection of analyte concentrations significantly below $10^{-10}$ molar. The waveguide structure of Sloper was of the gradient-index type, formed by diffusion of a dopant into the silica base, which results in a drop-off of dopant concentration with distance from the interface. The waveguide of Zhou had only a single "channel" (measurement region).

Therefore, a need exists for an optical structure useful in an evanescent sensing immunoassay, which provides increased levels of propagated TIR light and increased evanescent field intensity, as well as multiple measurement regions. Such an optical structure should desirably be capable of detecting of analyte concentrations of $10^{-13}$M and preferably below $10^{-15}$M. A need also remains for an immunosensor including such an optical structure, which is sufficiently inexpensive and practical to be produced as a commercial device, and which provides accurate and repeatable results in the hands of non-skilled persons. Still further, a need also remains for an biosensor capable of detecting ions, as opposed to just hormones or other biological molecules.

SUMMARY

The invention comprises a step gradient waveguide, also described as a composite waveguide, useful for performing evanescent sensing assays. The waveguide includes a thick substrate formed of a first optical material of refractive index $n_1$ and having a first surface, and a thin film formed of a second optical material having a refractive index $n_2$ which is greater than $n_1$, the thin film being disposed adjacent and in operative contact with the substrate. The optical substrate has a thickness which may be from about 0.3 μm up to 10 mm or more, depending on the material used, while the thin film has a thickness which is generally between about 0.3 μm and about 5 μm. Highly preferably, the waveguide thickness is selected to provide for internal propagation in from one to four modes only.

The invention further encompasses a kit comprising the composite waveguide, and at least one specific binding molecule immobilized to said thin film and constructed to bind with specificity an analyte. The kit may be further constructed for use in either a competition assay or a sandwich-type assay. The tracer molecule is further constructed to be excited by evanescent light penetrating from the thin film into an adjacent aqueous environment, and to respond thereto by emitting a photodetectable tracer signal.

In a preferred embodiment, the composite waveguide comprises the substrate with a plurality of thin strips of the thin film disposed in parallel array thereon, and the kit further includes a second solution containing a known concentration of analyte in a buffer.

In preferred embodiments of the composite waveguide, coupling means are integrally adapted and in operative contact with the thin film for coupling input light thereinto. One embodiment of coupling means is a grating etched into the substrate on the surface adjacent the thin film. Alternatively, instead of a physical grating, a grating-type coupler may be composed of an array of segments of a different refractive index $n_5$ disposed in the substrate in a regular spacing analogous to that of the ridges in a grating. In another alternate embodiment, a relatively thick waveguide coupler is disposed on the planar surface of the thin film waveguide opposite the substrate, near one end of the composite waveguide. The waveguide coupler is dimensioned and constructed of appropriate optical material so as to evanescently couple light propagated by TIR in a thick input waveguide across a thin spacing layer into the thin film waveguide.

In a highly preferred embodiment, the composite waveguide is constructed by vapor deposition of the thin film on the substrate, masking of the thin strips with a resist compound, and etching the thin film to expose the substrate in the unmasked areas. The resist compound is then removed to allow immobilization of the binding molecules to the thin strips.

The invention further embraces apparatus for performing specific binding assays, the apparatus comprising a composite waveguide together with an optical unit having a light source positioned to direct light into the waveguide for propagation by total internal reflectance therein, and detection means oriented to detect light from a region proximal to the optical structure.

The ("IOW") of the invention is capable of detecting analyte concentrations in the femtomolar ($10^{-18}$M) range. Such sensitivity is well beyond that achieved by other thin-film evanescent sensors, and also beyond the sensitivity expected solely on the basis of the increased reflection density intensity in the thin-film waveguide.

BRIEF DESCRIPTION OF THE DRAWINGS

In the drawings, which depict the best mode presently known for carrying out the invention.

DETAILED DESCRIPTION OF THE ILLUSTRATED EMBODIMENTS

Figure 2A:
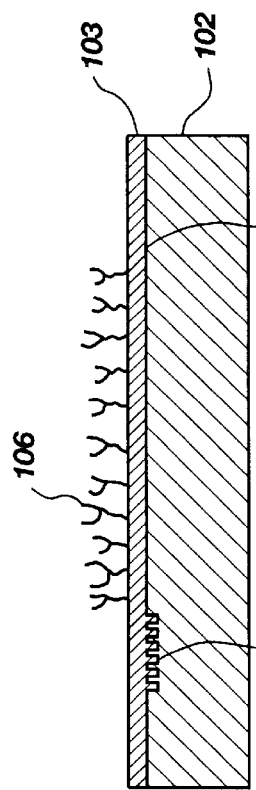
FIG. 2A is a side view of a composite waveguide having an integral etched grating coupler.

A composite waveguide indicated at 100 has a substrate 102 formed of a first optical material of refractive index $n_1$ (FIG. 1A), and a thin-film waveguide layer 103 of a second optical material of refractive index $n_2$, with $n_2$ being greater than $n_1$. The waveguide layer 103 has a plurality of binding molecules 106, each constructed to specifically bind an analyte, immobilized on the upper surface 103A. The substrate 102 has a thickness D1 which may be from about 0.3 μm up to 10 millimeters (mm) or more, while the thin-waveguide 103 has a thickness D2 of between about 0.3 microns (μm) and 5 μm. If the substrate 102 is relatively thick, perhaps 0.5 mm or more, as shown in FIG. 1A, it may also serve as a mechanical support in addition to having the optical properties necessary for supporting effective waveguiding of light in the thin film waveguide 103. However, in some embodiments it is preferred, generally for ease of manufacture, that the substrate 102 be comparatively thin. In such cases an additional support layer (not shown) may be added below the optical substrate 102 (not shown).

In a presently preferred embodiment, the substrate 102 is silicon dioxide, either in the form of a $SiO_2$ thin film laid down by vapor deposition or other techniques as known in the art, or in the form of quartz (here defined as including both natural quartz, and fused silica or other manmade quartz), with a waveguide layer formed of silicon oxynitride ($Si_2O_xN_y$, or, generally, "SiON"). The term "deposited $SiO_2$" is used hereinafter to distinguish the deposited $SiO_2$ from quartz/fused silica, etc. Silicon dioxide has a refractive index of n=1.47, and, if sufficiently pure, exhibits very low fluorescence. Silicon oxynitride is mechanically durable, transparent in the visible wavelength range, substantially non-fluorescent, and has a refractive index generally above 1.5 and reaching as high as 2.0 depending on the stoichiometric ratios of O to N. In a further presently preferred embodiment, the SiON is $Si_2O_3N$.

In another embodiment, the substrate 102 is formed of SiON having a refractive index $n_1$ and the waveguide film 103 is formed of SiON having a refractive index of $n_2$ wherein $n_2 > n_1$. The refractive index of the SiON compositions is controlled by the proportion of nitrogen. That is, the SiON of the substrate will have a lower proportion of nitrogen than the SiON of the waveguide film.

In still another embodiment, the substrate 102 is formed of $MgF_2$ (magnesium fluoride), refractive index n=1.38, and the waveguide layer 103 is a pure silicon dioxide thin film. Because the MgF substrate is formed by vapor deposition techniques or the like which are tedious and comparatively expensive, in this embodiment the substrate 102 need be only sufficiently thick to ensure efficient propagation of at least one guided mode. At present, the SiON waveguide layer 103 is preferred, as it provides better adherence to the substrate in aqueous solutions than the $MgF_2$ waveguide. However, the $MgF_2$ waveguide/$SiO_2$ composite waveguide may be entirely suitable for use with non-aqueous solvents.

In a presently preferred embodiment of a structure including a thin film SiON waveguide, the substrate 102 is a layer of $SiO_2$ deposited onto a silicon wafer support. This is preferred because the surface of the substrate 102 is much more uniform and smooth, which in turn produces much smoother planar surfaces in the deposited SiON film. The increased smoothness of the waveguide surfaces reduces the propagation losses by at least two-fold in comparison with a thin film waveguide deposited on a quartz or fused silica substrate.

Figure 1B:
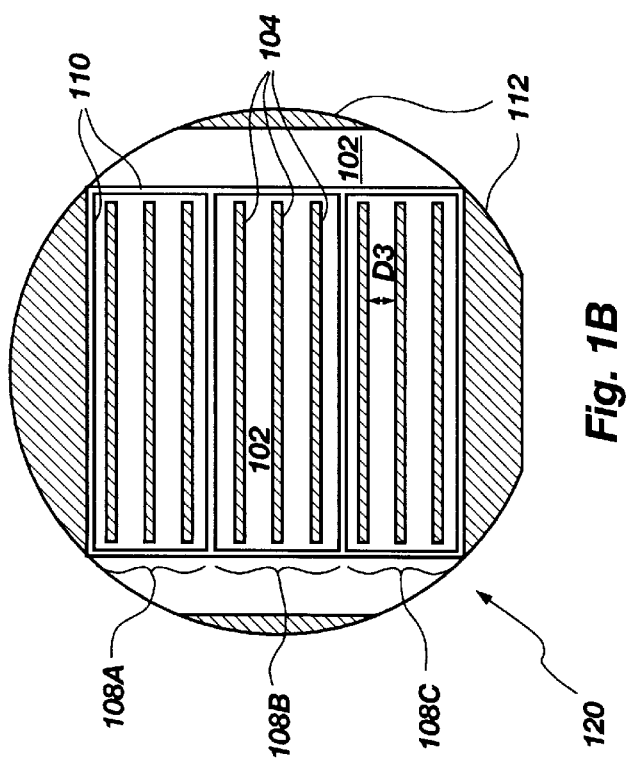
FIG. 1B is a top view of a composite waveguide module having a cross-sectional composition according to FIG. 1A.
Figure 1A:
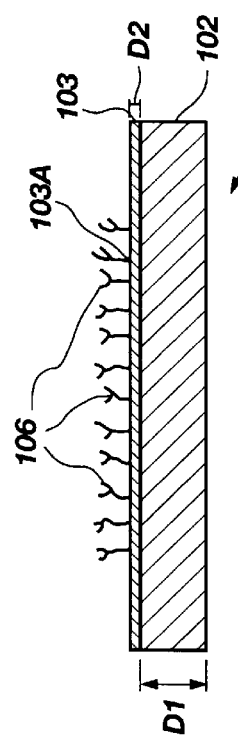
FIG. 1A is a side cross-sectional view of the composite waveguide of the invention.

In FIG. 1B, the waveguide layer is shown as a plurality of strips 104 which do not extend the full length of the substrate 102. This is an optional configuration of the waveguide layer designed to provide multiple waveguide "channels" for different sample solutions and/or for having different immobilized capture molecules. Further optionally, the composite waveguide 120 may be configured as a plurality of rectangular wells 108A, 108B, 108C, each containing three strips 104. The strips 104 are separated from one another by a distance D3 of at least about 5 mm. The wells 108A,B,C are separated by walls 110 extending upward from the substrate 102. The device of FIG. 1B may be formed by vapor deposition of the SiON over the entire surface of the substrate 102, masking the regions corresponding to the thin strips 104 with a resist compound, etching the exposed SiON to remove it from the substrate 102, and removing the resist compound. In FIG. 1B, shaded regions 112 represent areas of the waveguide which were not exposed to etchant. The binding molecules 106 are then immobilized to the thin strips 104. This can be accomplished by means known in the art of binding assays. Alternatively, the the wells 108A, 108B, 108C may be configured for flow-cell type operation, as separate flow-through compartments for background, calibration known analyte concentration), and test sample (unknown) solutions.

High quality composite waveguides made of the material combinations described above can be formed using plasma enhanced chemical vapor deposition (PECVD) to deposit a thin film over an entire surface of the substrate, and then lithographically etching away the thin film except in the desired strips. In the case of SiON, the PECVD is performed with a mixture of nitrogen, nitrous oxide, ammonia and silane gases, and the stoichiometry of $Si_zO_xN_y$ is varied by changing the respective partial pressures of the above components.

For the lithographic steps, it is presently preferred to use a reactive-ion etch (RIE) process with commercially available photoresist compounds. The areas of the film which are to become the strips or channels are coated with the resist, and the surrounding areas are etched down to the substrate. In the present embodiment, the DUV negative-tone photoresist XP89131 available from Shipley Co. is preferred, and the etchant is a plasma of $O_2$ and $CHCl_3$ gases. Positive tone resists such as XP2198 (Shipley Co.), APEX-E from IBM, and CAMP6 from OCG are also suitable. (All of these compositions are proprietary). All of these resist compounds are of the chemical amplification type, comprised substantially of phenolic polymers. While older photo-resists such as PMMA (polymethylmethacrylate) could be used, the chemically amplified DUV resists are considered to produce superior results for the present purposes.

Almost any other etching technique could be readily applied for etching the channels into the waveguide film, including plasma etch, ion milling, or a wet etch. However, where it is desired to use a substrate-etched grating to increase the coupling efficiency (see FIG. 2A and related description), the RIE process is preferred. This is because the etching process is critical to production of a highly anisotropic grating. RIE etching is believed to provide the best results for the grating, and wet etching would be unsuitable. For waveguides having an etched grating coupler, then, it is convenient to use the RIE process to etch the channels as well.

It is also within contemplation that the thin-film waveguide channels could be produced by a wet lift-off process. In this process, the substrate of the waveguide would be masked to leave the channel regions bare, and the SiON thin film would then be deposited over the whole surface including the masking agent. After deposition of the film, the entire surface would be immersed in a solvent selected to "lift-off" or remove the mask, together with the waveguide film deposited on the mask, while leaving the film deposited on the bare quartz.

All steps of the waveguide fabrication should be performed in an extremely clean environment, preferably a clean-room meeting the standards of at least class 10.

EXAMPLE 1

SiON Composite Waveguide Fabrication

Waveguides comprising a 1 μm thick film of $Si_2O_3N$ on $SiO_2$ have been produced as follows. A heated sample holder containing a 4 inch quartz wafer was placed in a plasma-enhanced chemical vapor deposition (PECVD) reactor. Process gasses flowed from the perimeter of the PECVD vessel, over the sample, and were then pumped out of the vessel through a central port. During deposition, the PECVD reactor was maintained at 300° C. and 1.25 Torr, with 50 W of power to a 13.56 MHz generator. The gas mixture consisted essentially of 27 standard $c^3$ per minute (sccm) silane ($SiH_4$), 500 sccm nitrogen, 200 sccm ammonia, and 1300 sccm nitrous oxide. The respective inlet partial pressures were approximately 17 mTorr, 308 mTorr, 123 mTorr, and 802 mTorr. Under these conditions, the deposition rate was about 590 Å/minute and a 1 μm film was produced in about 15 minutes. These silicon oxynitride films had an approximate elemental ratio of Si:O:N=2:3:1, and at refractive index of about n=1.53 to 1.54.

Next, the $Si_2O_3N$ films were coated with photoresist, masked, and developed to expose all but nine parallel 1 mm×65 mm strips of the SiON film separated by 5 mm. The unmasked SiON was etched down to the quartz wafer. The photoresist was stripped, and the etched wafer was cleaved to produce three 23 mm×69 mm rectangular pieces, where each piece contained three parallel 1 μm thick channel waveguides. Only the two outside channels were used in the assays described here.

There are several properties of composite waveguides which can be correlated to their relative suitability for evanescent-sensing biochemical binding assays. These include the ability to withstand the solvent used in the assay, which is generally but not always water; the amount of propagated light lost per unit distance traveled in the waveguide ("propagation loss", expressed as dB per cm; the intrinsic level of fluorescence of the waveguide upon irradiation with light of the excitation wavelength to be used, as measured within the bandwidth of the tracer fluorescence emission; reflections/cm at the waveguide-superstrate interface ($N_r$); and adequate depth of evanescent penetration ($d_p$).

EXAMPLE 2

Characterization of SiON Waveguide

Scanning electron microscopy was used to examine the shape and thickness of etched channel waveguides. A nominal channel should have optically smooth, rectanglar edges and a uniform thickness. For optical characterization of channel waveguides, the beam of the 632.8 nm line from a HeNe laser was coupled into the waveguide using a prism coupler. In a typical experiment, values were determined for waveguide thickness ($t_{wg}$), refractive index ($n_{wg}$), internal reflection angle ($q_{wg}$), reflections/cm at the waveguide-superstrate interface ($N_r$), depth of penetration ($d_p$), and propagation loss (dB/cm). The data of Table 1 summarize the properties measured for a typical SiON waveguide constructed by the procedure outlined

TABLE I

Optical characterization of SiON waveguides

| waveguide parameter | air superstrate | water superstrate |
|---|---|---|
| $t_{wg}$ (μm) | 1.31 ± 0.11 | N.A. |
| $n_{wg}$ | 1.53 ± 0.0 | N.A. |
| propagation loss (CdB/cm) | 0.76 ± 0.09 | N.D. |
| $q_{wg}$ (degrees) | 82.67 ± 0.47 | 82.85 ± 0.42 |
| $d_p$ (nm) | 44.10 ± 0.06 | 68.79 ± 0.29 |
| $N_r$ (reflections/cm) | 492.10 ± 71 | 479 ± 0.29 |

Each parameter was measured for three different channel waveguides with air as the superstrate. The mean and standard error of these measurements is reported. In addition, the last three pararneters ($q_{wg}$, $d_p$, N) were determined when water was substituted for air as the superstrate.
N.D. - not determined.

in Example 1. Also, these waveguides possess a high degree of physical definition and the desirable features of low propagation loss and minimal intrinsic waveguide fluorescence.

EXAMPLE 3

Fabrication of $MgF_2$/$SiO_2$ Composite Waveguide

The $SiO_2$/$MgF_2$ laminates were deposited in situ by electron beam evaporation, using a multipocket electron beam gun in a Balzers BAK760 high-vacuum coater. The deposition chamber was evacuated to 2 μTorr, and the silica chips used as mechanical supports on which the laminates were deposited were heated to 200° C. The chamber pressure rose to 3.8 μTorr as a result of heating of the silica chips prior to deposition. The source materials, 99.9% pure $MgF_2$ and 99.999% pure $SiO_2$, were placed in molybdenum- and graphite-lined hearths, respectively, in the rotatable source carousel. Both source materials were brought to the deposition temperature with the shutter closed. First the $MgF_2$ was evaporated with a slowly sweeping 10-kV (kilovolt) electron beam (≈12 mm² elliptical spot size) followed by similar evaporation of the $SiO_2$. The deposition rates of $MgF_2$ and $SiO_2$ were controlled at 20 Å/s and 10 Å/s (angstroms per second), respectively, by means of an oscillating crystal monitor. A 0.36 μm film of $MgF_2$ was deposited in 3 minutes, and a 1.0 μm film of $SiO_2$ was deposited in 16 minutes.

Following construction of the physical portion of the waveguide, a plurality of specific binding molecules, that is, molecules having the property of specifically binding a chosen analyte, are immobilized on the surface of the thin film waveguide channel(s). Such specific binding molecules may be antibodies, receptor molecules, and the like, or fragments thereof that are operative to specifically bind the corresponding analyte. Converse pairs, e.g. such as an antigen for detecting certain antibodies with the analyte being the antibody, are also suitable. Other types of binding molecule/analyte pairs will be apparent to those of ordinary skill, as will means for immobilizing the binding molecule. Presently preferred means for immobilizing the binding molecule are discussed subsequently herein.

Figure 4A:
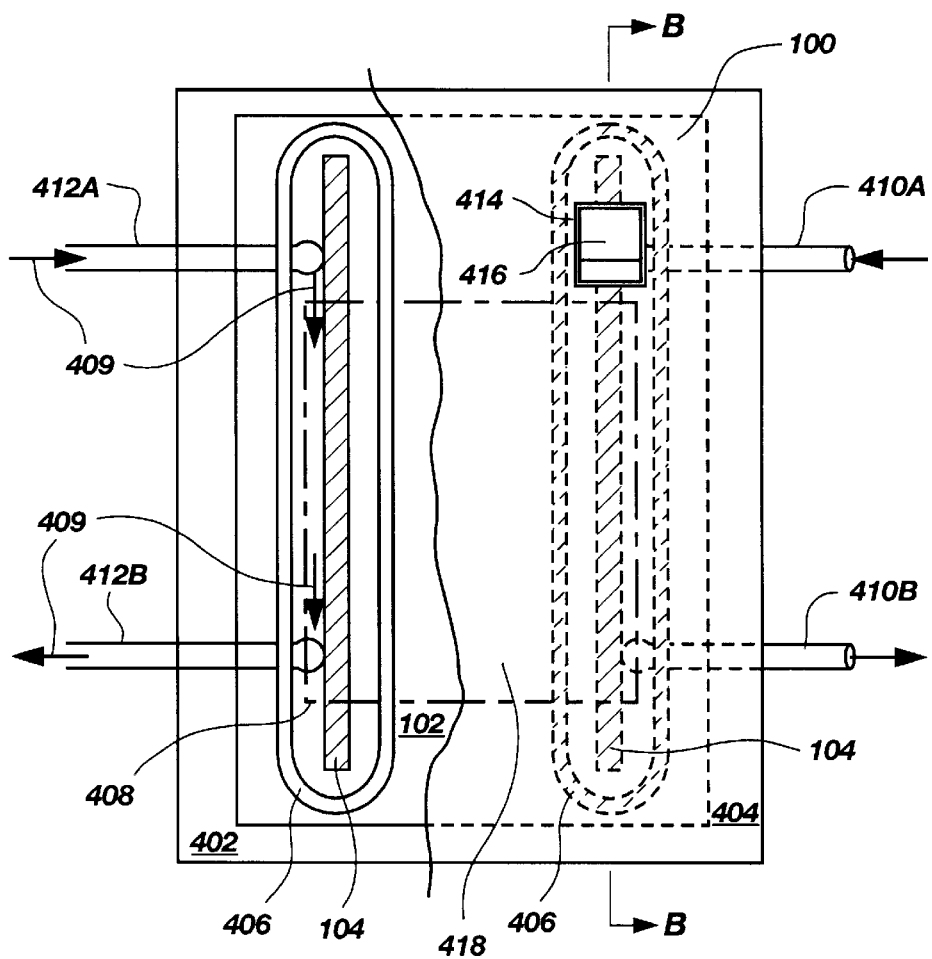
FIG. 4A is a schematic diagram of a top view with partial cutaway of a flow cell incorporating a multichannel composite waveguide.
Figure 4B:
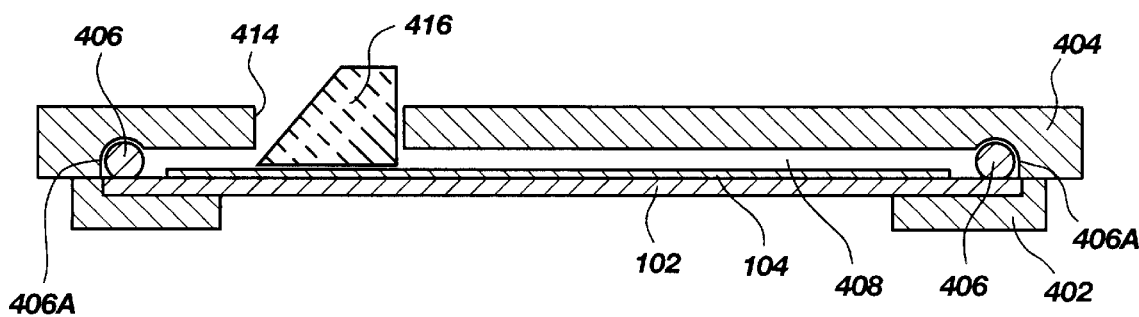
FIG. 4B is a side cross-section taken along line B—B of FIG. 4A.

A flow cell incorporating a two channel waveguide fabricated and characterized as in Examples 1 and 2 is shown in FIGS. 4A and 4B. A composite waveguide 100 is held between a bottom plate 402 and a top plate 404 spaced by a pair of black silicone rubber o-ring gaskets 406 (FIG. 4B). Each gasket is seated in a corresponding groove 406A milled in the top plate, and forms a longitudinal flow channel 408. The flow channels have respective inlet ports 410A, 412A and outlet ports 410B, 412B. Arrows 409 indicate the direction of flow of liquid through the channel 408. Each flow channel also has a hole 414 for placing a coupling prism 416. The interior of the bottom plate has a window 418 milled therein to support the waveguide and provide a clear view of the waveguide bottom through the silica chip support layer. The aluminum parts of the entire flow cell are desirably flat black, to absorb stray light. Coupling prisms (4 mm wide by 10 mm high truncated 45-45-90 LASF prisms, $n_p$=1.83, obtained from Karl Lambrecht Co. were fixed in place inside the windows 414 with GTE 118 RTV silicone rubber cement. A series of finger screws (not shown) were used to clamp the top and bottom plates 404, 402 to the substrate 102, and to maintain coupling pressure on the prisms 416. Polyethylene screw-in tubing connectors, TEFLON® microtubing, and disposable syringes served as the sample delivery system (not shown). The sample volume of each channel 408 was 300 μL.

Prism coupling the waveguide with aqueous superstrate comprises placing the waveguide on the bottom plate of the flow cell, wetting the waveguide surface opposite the substrate with buffer solution to be used in measurements, and then placing the top plate with the attached prisms over the wetted waveguide. An advantage of the raised-channel waveguide structure is that effective prism coupling is easily accomplished by placing mild pressure on the coupling prisms.

Evanescent binding assays in two model systems were performed with the flow cell of FIGS. 4A, 4B, using a dual-channel assay format similar to that described by Herron et al. in "Fluorescent immunosensors using planar waveguides", *SPIE Vol. 1885* (*Advances in Fluorescence*

Sensing Technology), pp. 28–39, 1993, as well as in the copending U.S. patent applications Ser. Nos. 08/064,608 and 08/263,522.

EXAMPLE 4

Model Assays Using Thin-Film Waveguide Flow Cell

In the first or direct-binding model system, the binding of a biotinylated antibody labelled with a fluorescent tracer to avidin immobilized on the waveguide surface was measured. The particular antibody used was an anti-fluorescein antibody designated 9-40, produced by standard hybridoma methodology. The 9-40 antibody was labelled with the dye Cy-5 ($\lambda_{abs,max}$=650 nm, $\lambda_{cm,max}$=667 nm, $e_{max}$=2×10$^5$ M$^{-1}$ cm$^{-1}$) according to the manufacturer's procedure (Biological Detection Systems). The labeling efficiency was approximately four dyes per protein molecule. An untreated hydrophilic SiON IOW surface was treated for 8 hr with a 0.2 mg/mL solution of avidin (obtained from Sigma) dissolved in phosphate buffered saline (PBS, pH 7.4), to physically adsorb the avidin to the waveguide surface.

A portion of the Cy-5 labeled 9-40 was biotinylated using N-hydroxy-succinimidobiotin (Sigma). Specifically, a 20-fold molar excess of this reagent was added to a 1 mg/mL solution of 9-40 in 0.1M sodium carbonate/sodium bicarbonate buffer, pH 9 (CBB). This mixture was allowed to react for 2 hr at room temperature, and the product (biotinylated, CY-5-conjugated 9-40) was purified by gel permeation chromatography using a PD-10 column (Pharmacia) equilibrated in PBS.

The second type of assay was an indirect, sandwich type assay in which the binding of free fluorescein-conjugated BSA to immobilized anti-fluorescein antibody (antibody 9-40) was measured using an anti-BSA antibody conjugated with Cy-5 as a tracer. The IOW surfaces with immobilized 9-40 antibody was prepared as follows. Prior to immobilization, 9-40 was acid pre-treated in citrate buffer (pH 3) for 1 hr and reconstituted in PBS at a concentration of 2.3×10$^{-7}$M (0.03 mg/ml), following the procedure described by Lin et al. (1989). SiON IOWs were treated with 1% dichlorodimethylsilane (DDS, Sigma), rinsed three times in deionized water, and then immersed in a solution of the acid-pretreated antibody 9-40 for 3 hr at room temperature.

Murine monoclonal anti-bovine serum albumin antibody (anti-BSA; available from Sigma) was labeled with Cy-5 as described for antibody 9-40. Bovine serum albumin (Sigma) was labeled with fluorescein isothiocyanate (FITC, Sigma). A 20-fold molar excess of FITC was added to a 1 mg/ml solution of BSA in CBB. This mixture was allowed to react for 1 hr at room temperature, and the conjugate was purified using a PD-10 column equilibrated in PBS. Labeling efficiency was approximately 2 FITC groups per BSA molecule. It should be noted that since the assays were performed with excitation at 632.8 nm, a wavelength which well exceeds the absorption band of FITC ($\lambda_{abs,max}$=492 nm), the FITC here serves solely as a hapten for 9-40, and not as a fluorescent tag.

Figure 5:
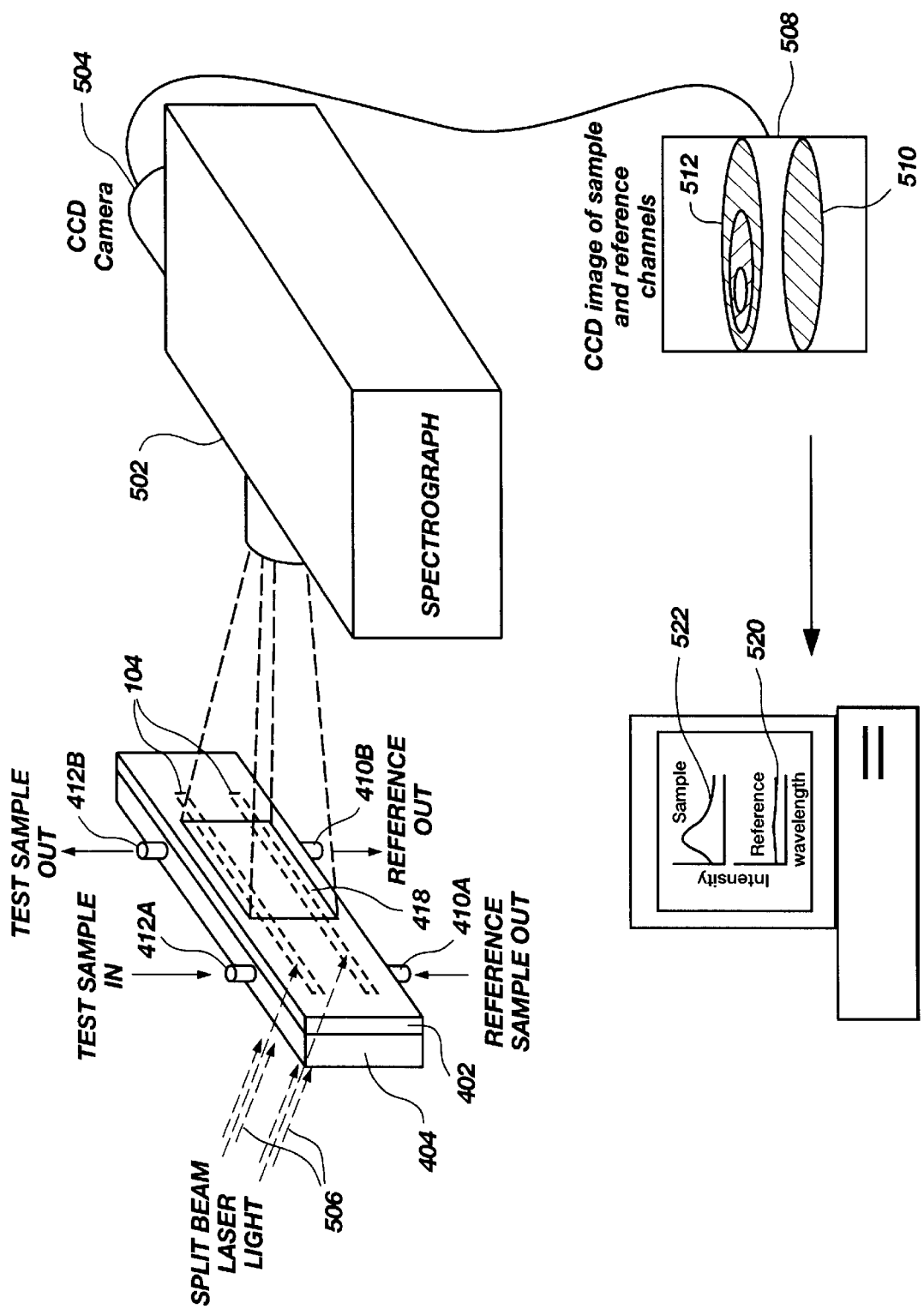
FIG. 5 is a schematic diagram of optical apparatus including the flow cell of FIGS. 4A and 4B, for performing binding assays therewith.

To perform the assays, IOWs coated as described in the preceding paragraphs were mounted in a flow cell like that of FIGS. 4A and 4B; and placed on a rotating goniometer (not shown) in the collection path of a spectrograph 502 associated with a CCD camera 504 (FIG. 5). The goniometer is optional, but useful in an experimental set-up to ascertain the best coupling angle for coupling the laser beam into the waveguide. Once the best coupling angle has been determined and the apparatus standardized, a goniometer is not required to perform the assay. The input light was the red line (6 mW at 632.8 nm) of a HeNe laser (made by Melles Griot), split into dual beams 506, and simultaneously prism coupled into two channels 104 of the composite waveguide. In this manner, a reference channel and a sample channel were excited.

For detection, the 1 mm wide guided modes in each channel were oriented perpendicular to the entrance slit of the spectrograph. Light emitted from a 1 mm long section of the two parallel streaks was imaged through the window 418 in the bottom plate 402 of the flow cell with a 50 mm f/5.6 camera lens onto the slit of spectrograph 502. The collected light emission was wavelength-dispersed using a single grating monochromator 502 (SPEX 1681c Minimate-2, f/3.9, 300 grooves/mm) centered at 700 nm, and directed onto a thermoelectrically-cooled CCD detector 504 (Photometrics Series 200), producing an image 508 containing reference region 510 and sample region 512. The reference and sample image regions 510, 512 were separately binned and vertically integrated and converted on a MACINTOSH IIx computer to reference spectrum 520 and sample spectrum 522, respectively, of intensity vs. wavelength.

Both assays followed the same general scheme: 1) a capture protein was immobilized to the surface of both the sample and reference channels; 2) aliquots of the hapten-carrier protein conjugate (with fluorescent tracer) were added to the sample channel; and 3) the same concentration of fluorescent tracer (without hapten) was added simultaneously to the reference channel.

Each measurement began by collecting the baseline spectra of PBS buffer in both the sample and reference channels. Starting with the most dilute analyte solution, 1 mL of the sample and reference solutions described in Table 1 were injected into the flow cell. The solutions were incubated with the waveguide surface for 2 min for assay 1 and 5 min for assay 2, followed by collection of 10 sec spectrograph images of both channels. This process was repeated several times until the most concentrated solution was assayed. All CCD images were collected without a wash step; i.e., with the fluorescent analyte filling the sample and reference channel volume. Reference and sample spectra derived from each CCD image of each measurement were integrated from 653 nm to 693 nm. Binding curves were constructed from these data by taking the ratio of the integrated intensity of the sample to that of the reference, and then plotting these ratios as a function of bulk analyte concentration. Such ratiometric measurements compensated for two effects: non-specific binding of the tracer, and parasitic excitation of bulk fluorescence.

Figure 6A:
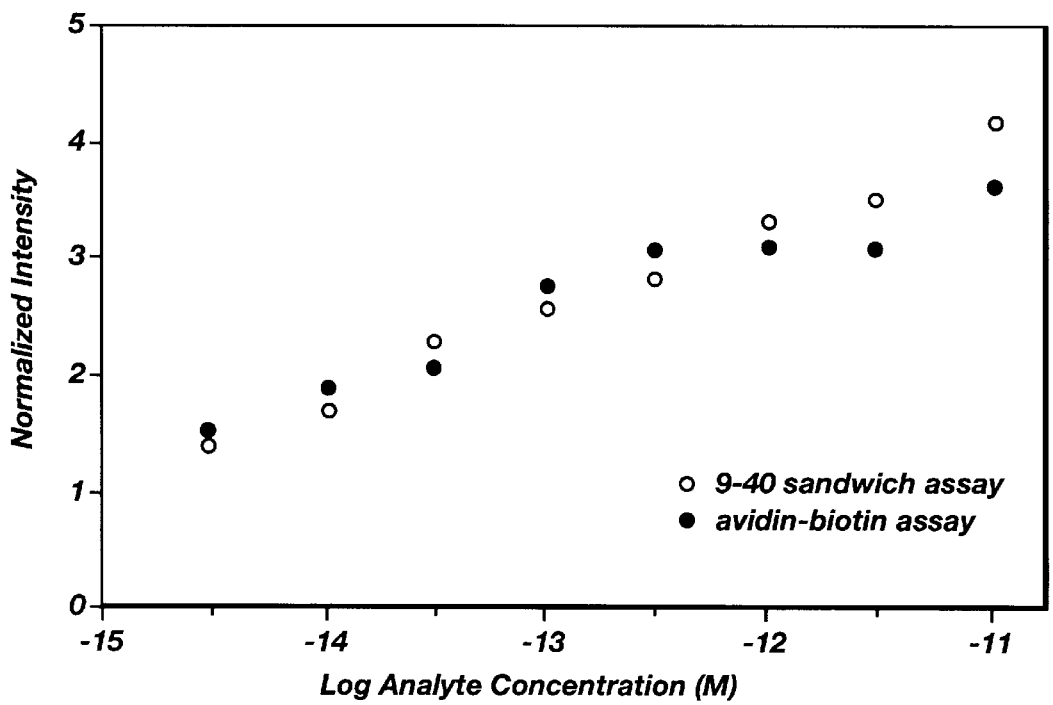
FIGS. 6A and 6B are charts of fluorescence measurements made with the apparatus of FIG. 4.
Figure 6B:
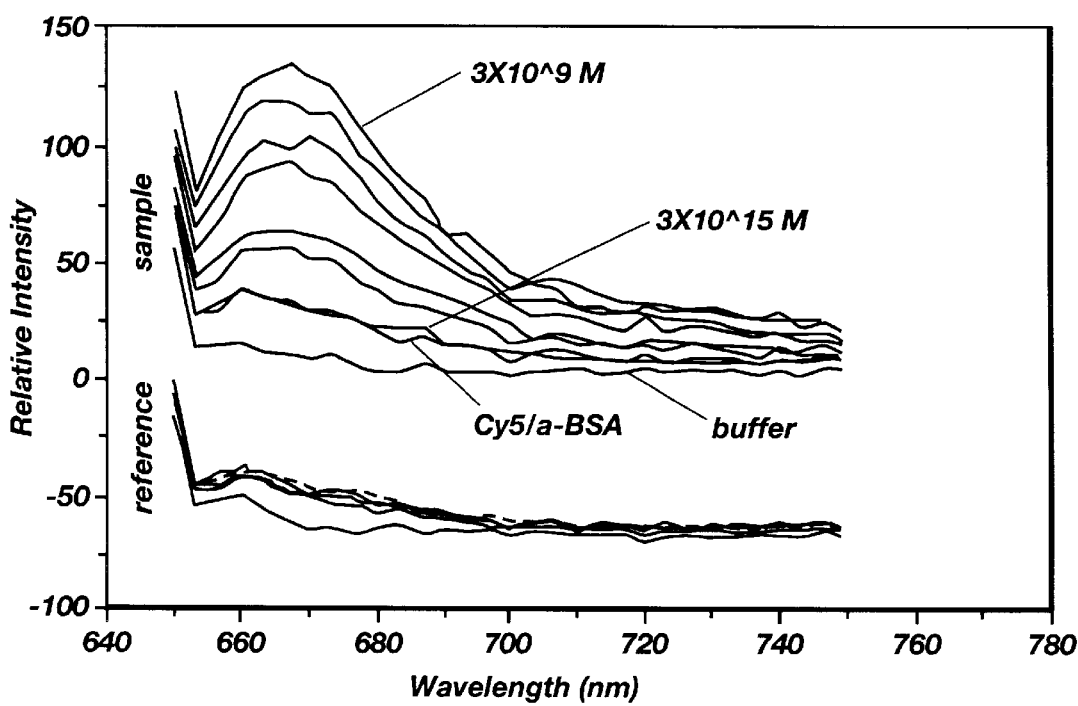

The results obtained with the two assay schemes are shown in FIGS. 6A–6B. The results indicate that analyte could be detected at concentrations as low as 3×10$^{-15}$M with a two-channel Si$_2$O$_3$N thin film waveguide flow cell. These measurements are at least 3.3×10$^4$ times more sensitive than the thin film waveguide immunosensors reported by Sloper et al. or Zhou et al., op cit., and at least 33 times more sensitive than the thick film sensor of Herron et al. 1993, op cit.

The prism coupling scheme described in Example 4 is efficient, simple, and well suited for use in laboratory experiments. However, such a device is relatively expensive, and thus less than ideal for a disposable IOW module for use with a point-of-care optical unit. Further, the prism coupling scheme requires precise pressure on the prisms and precise alignment of the incident laser beam.

An alternate embodiment of a coupling scheme, which avoids these problems, is to provide a diffraction grating etched either into the surface of the waveguide opposite the substrate, or into the substrate adjacent the waveguide. The presently preferred embodiment is that of a substrate-etched grating. As seen in FIG. 2A, the substrate 102 has a grating 200 etched into the surface 102A which is in contact with the thin film 103. The binding molecules 106 are immobilized down-beam of the grating 200. Optionally, a second grating (not shown) may be etched into the substrate 102, down-beam of the immobilized binding molecules. Such a second grating is for purposes of optical characterization of the waveguide, and is not required for purposes of the fluorescence binding assay.

The depicted substrate-etched grating is advantageous in that the light can be conveniently in-coupled from the back side of the device, and without interference from macromolecules bound to the waveguide surface. Also, it is convenient and economical from a manufacturing perspective to etch the grating into the substrate prior to deposition and etching of the channel waveguides.

Figure 2B:
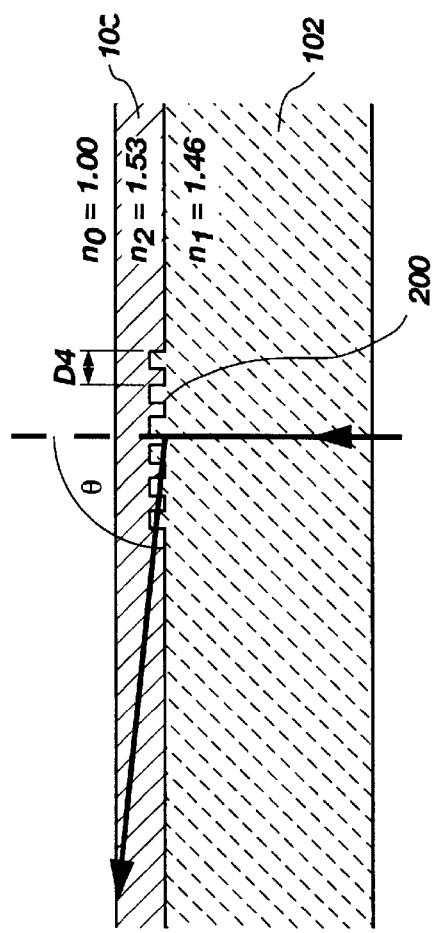
FIG. 2B is a schematic illustration of the embodiment of FIG. 2A showing diffraction of normal incident light beam into a guided mode of the thin film waveguide.

The efficiency of light incoupling by the etched grating will vary according to the spacing, the profile or blaze, and the aspect ratio of the grooves. These parameters should be optimized according to the wavelength of the input (excitation) light, the index of refraction of the superstrate, and the waveguide thickness, by techniques conventional in the art. In the present case, a grating period D4 of about 0.42 μm was computed for coupling of a normally incident 632.8 nm laser beam into the m=0 mode of the thin film SiON waveguide (θ=83°; see FIG. 2B).

Figure 3A:
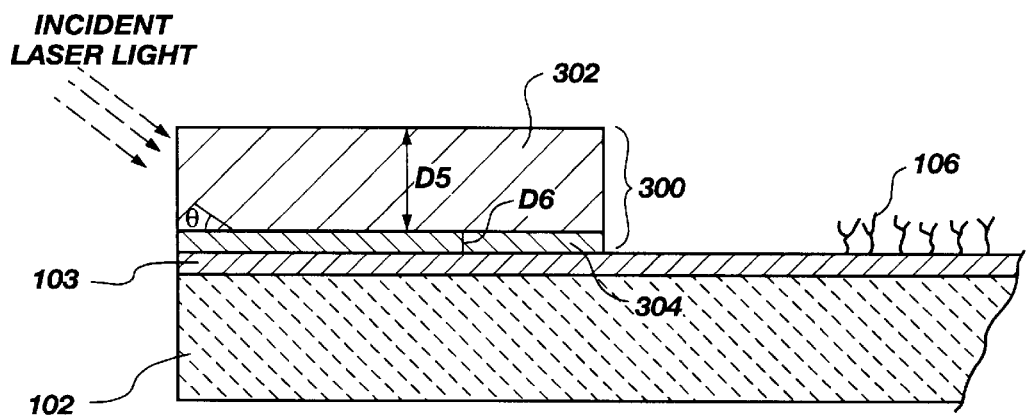
FIG. 3A is a side cross-sectional view of an alternate embodiment of a composite waveguide, having an integral waveguide coupler.
Figure 3B:
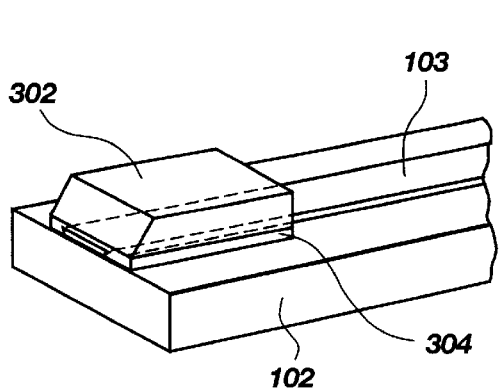
FIG. 3B is a perspective view of the embodiment of FIG. 3A.
Figure 3C:
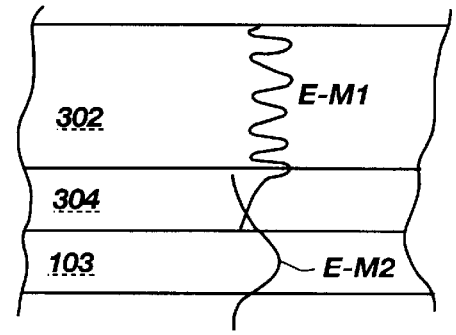
FIG. 3C is a schematic illustration of the overlap of the evanescent electromagnetic fields of the input waveguide and the thin film waveguide.

Still another coupling scheme uses the principle of evanescent penetration to evanescently couple light from a waveguide coupler into the composite waveguide across a precise spacing layer (FIGS. 3A, 3B and 3C). The waveguide coupler is contactingly mounted on the upper surface of the composite waveguide, adjacent the exposed surface of the thin film. Like the prism coupler, the waveguide coupler does not extend into the region to which the specific binding molecules are immobilized.

As seen in FIG. 3A, a waveguide coupler 300 comprises an input waveguide 302 which consists of a comparatively thick (1 mm or greater) layer of material of refractive index $n_3$, and a thin spacing layer 304 of refractive index $n_4$, where $n_4$ is less than both $n_3$ and $n_2$. The input waveguide has a receiving edge for receiving the input laser light, and a thickness D5 which is sufficient to allow easy end coupling of the input beam into the receiving edge. The spacing layer has a thickness D6 selected to maximize the evanescent coupling of waveguided light from the input waveguide into the thin film of the composite waveguide.

According to coupled mode theory, light propagating in one waveguide can be synchronously coupled into an adjacent waveguide if there is overlap between the evanescent regions of the two waveguides in the low index region separating them (FIG. 3C). The efficiency of coupling depends upon the spacing between the guides, the respective modal propagation constants, and the distance of the interaction. Since the coupling efficiency varies according to the cosine of the distance of interaction, in theory it will reach 100% at a certain length. Therefore, the synchronous evanescent coupling device should be quite efficient.

To achieve maximum coupling efficiency, the spacing layer thickness should be adjusted such that $K_1 = (j+1)\pi/2, \ (j=0, 1, 2 \ldots)$ where K is the coupling constant and depends on the refractive indices $n_1$, $n_2$, $n_3$, $n_4$, the wavelength lambda of the input light, and the respective thicknesses D2, D5 and D6 of the thin film waveguide, the input waveguide, and the spacing layer. With the thin film waveguide, it should be taken into account that generally, only one or a few of the lowest modes (preferably from j=0 to about j=10, and no more than j=20) are being propagated in the waveguide. Preferred waveguide couplers are configured to increase the proportion of laser light which is propagated in these lower modes.

For a silicon oxynitride composite waveguide, the spacing layer can be made of $SiO_2$. Desirably, the spacing layer 304 is deposited epitaxially, so that its thickness can be controlled very accurately at the time of deposition. The input waveguide 302 is attached on top of the spacing layer, after all epitaxial processing and etching steps have been finished in the fabrication of the composite waveguide. The input waveguide is made of a high refractive index material such as rutile, zirconia, or a high-index glass, and may be adhered to the spacing layer 302 by an index-matching cement of refractive index near $n_3$. This assembly would be comparatively inexpensive, and is thus attractive for a disposable, one-time use module.

Preferably, as shown in FIG. 3A, the laser light is focussed into the receiving edge of the input waveguide at an angle θ' which is a degree or two less than the critical angle for TIR at the interface between the input waveguide and the spacing layer. Such angled beam entry has been found to substantially increase the proportion of internally propagated light in the evanescent tail, and thus the evanescent intensity.

Figure 7:
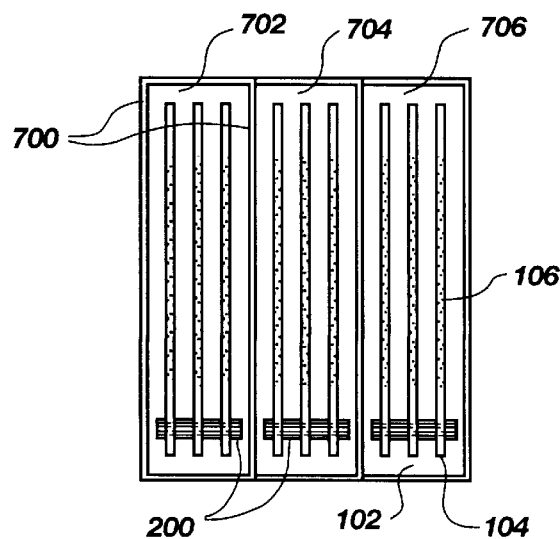
FIG. 7 is a top view of an alternate embodiment of a composite waveguide, having etched sample wells.

Still another embodiment is an IOW with integrally formed sample wells 702, 704, 706 (FIG. 7), each of which may contain multiple thin waveguide channels 104. In a preferred embodiment, walls 700 which enclose the wells are formed by layering a submicron cladding film of the substrate optical material on the composite waveguide, appropriately masking, and then etching the cladding back down to the SiON waveguide layer. These steps are performed prior to immobilization of the specific binding molecules. Sample wells thus constructed provide physically defined regions in which either different antibodies can be immobilized, or to which different solutions, e.g. background or control samples vs. test samples, can be added. The same technique could be used to form open-ended longitudinal flow channels instead of the box-shaped reservoirs illustrated. Also, instead of layering the reservoir wall material over the composite waveguide, the same technique could be used to form reservoir or flow channel walls on a separate top plate.

At present it is believed that two additional factors related to the chemistry of immobilization of specific binding molecules to the waveguide surface can affect the sensitivity achieved. These are 1) the relative amount of non-specific protein binding to the thin-film surface (including the walls of any sample wells); and 2) the analyte/tracer-binding capacity of the immobilized binding molecules.

In a highly preferred embodiment of the multi-channel IOW, the IOW surface is treated to minimize non-specific binding which otherwise can cause significant overlap of tracer signal between channels. The problem of such overlap worsens rapidly with increasing numbers of channels per IOW. Take as an example a six-channel waveguide divided into three adjacent-channel pairs in three corresponding separate wells, with anti-CK-MB immobilized to one member of each pair and anti-CK-MM immobilized to the other member. The IOW so constructed would permit simultaneous calibrated measurement of binding of 2 different analytes, CK-MB and CK-MM. If the level of non-specific binding is assumed to be about 5% of the specific binding level, the channel with anti-CK-MB covalently attached will be contaminated to about 5% with non-specifically adsorbed anti-CK-MM. Conversely, the channel with anti-CK-MM will be contaminated to about 5% with non-specifically adsorbed anti-CK-MB. Thus, with such a 2-analyte IOW there could be about 10% crosstalk between the channels, already an undesirable contribution to background level. For a 4-analyte IOW (twelve channels), however, the background contributed by such crosstalk would increase to about 30%, which would seriously impair detection sensitivity. Obviously the problem worsens with increasing numbers of different analytes.

For this reason, it is highly desirable that the channels be coated with a coating that reduces non-specific binding to 1% or less of specific binding, prior to covalent immobilization of the specific binding molecule.

A method of enhancing the number of available analyte binding sites is to site-specifically immobilize the analyte binding molecules. For antigen-binding fragments such as F(ab')$_2$'s, this can be accomplished by providing a base coating having pendant maleimido groups. The F(ab')2 fragments are then reduced to yield Fab' fragments which contain a free thiol group at their C-terminal end, and this thiol group readily reacts to covalently couple the F(ab')$_2$ fragment to the maleimido group. Desirably, the coating with pendant maleimido groups also provides the inhibition of non-specific binding discussed in the preceding paragraph; this may for example be accomplished by a base coating comprising chains of polymerized hydrophilic residues adhered via a silica-affinic moiety to the waveguide surface, as disclosed by the copending U.S. patent applications Ser. Nos. 08/064,608 and 08/263,522. Protocols for achieving both of these methods can be found in the noted copending applications, and in the literature in Herron et al., "Fluorescent immunosensors using planar waveguides", *SPIE* 1885:28–39, 1993. Preferably, at least 70% of the immobilized analyte binding molecules should be available for binding.

It will be apparent that details of the composite waveguide can be varied considerably without departing from the concept and scope of the invention. The claims alone define the scope of the invention as conceived and as described herein.

What is claimed is:

1. A kit for performing specific binding assays, which kit includes:
  a biosensor comprising:
    a step gradient waveguide including a planar substrate formed of a first optical material of refractive index $n_1$, said planar substrate having a surface disposed adjacent to and in direct contact with a waveguide film formed of a second optical material having a refractive index $n_2$ which is greater than $n_1$; and
    at least one specific binding molecule immobilized to said waveguide film and configured to bind, with specificity, an analyte.

2. The kit of claim 1, wherein said second optical material is selected from the group consisting of: silicon oxynitride of refractive index $n_2$, and deposited silicon dioxide; and said first optical material is selected from the group consisting of: deposited silicon dioxide, quartz or fused silica, silicon oxynitride of refractive index $n_1$, and magnesium fluoride.

3. The kit of claim 2, wherein said waveguide film is configured as a plurality of parallel strips of said second optical material spaced from one another along the surface of the planar substrate and constituting a plurality of waveguide channels, and further having a plurality of different species of said specific binding molecules immobilized to said waveguide film, with each of said waveguide channels having a different one of said species immobilized thereto.

4. The kit of claim 2, wherein the surface of the planar substrate further includes a grating formed thereon, said grating being constructed to facilitate coupling of light from an incident excitation beam into said waveguide film.

5. The kit of claim 1, wherein said waveguide film is coated with a coating which provides a level of nonspecific protein binding which is less than about 10% of the amount of specific binding of said analyte, said coating being selected from the group consisting of: polymethacryloyl polymer, polyethyleneglycol, and avidin; and wherein said capture molecules are immobilized to said waveguide film by binding to said coating.

6. The kit of claim 1, wherein said step gradient waveguide is manufactured by a process of manufacture including the steps of:
  providing a piece of the first optical material having a surface;
  vapor depositing the second optical material onto said surface to a depth of between about 0.1 μm and 10 mm to produce a waveguide film layer;
  coating at least one region of said waveguide film layer with a resist compound which resist compound resists an etchant to produce a coated region and an uncoated region; and
  etching said waveguide film layer with an etchant to remove said second optical material from said uncoated region to produce the waveguide film.

7. The kit of claim 6, wherein said second optical material is selected from the group consisting of: silicon oxynitride of refractive index $n_2$, and silicon dioxide; and said first optical material is selected from the group consisting of: deposited silicon dioxide, quartz or fused silica, silicon oxynitride of refractive index $n_1$, and magnesium fluoride.

8. The kit of claim 6, in whose manufacture said step of coating at least one region with a resist compound comprises coating a plurality of parallel strips along said surface with said resist compound thereby producing a plurality of waveguide channels, and wherein a plurality of different species of said specific binding molecules are immobilized to said waveguide film, with each of said waveguide channels having a different one of said species immobilized thereto.

9. The kit of claim 8, whose process of manufacture further includes a step of etching a plurality of spaced grooves into said surface of said first optical material prior to said step of depositing said waveguide film layer, wherein said spaced grooves are oriented substantially perpendicular to said plurality of waveguide channels, and wherein spacing of said spaced grooves serves as a grating facilitating efficient coupling of light from an incident excitation beam into said waveguide film.

10. The kit of claim 1, wherein said second optical material is silicon oxynitride having an elemental ratio of approximately $Si_2O_3N$.

11. The kit of claim 1, wherein said step gradient waveguide further includes a waveguide coupler contactingly disposed on said waveguide film, said waveguide coupler comprising:
- an input waveguide formed of an optical material having a refractive index $n_3$, and having a thickness which is between about 0.5 mm and about 5 mm; and
- a spacing layer formed of an optical material having a refractive index $n_4$, wherein $n_4<n_3$ and $n_4<n_2$, and having a thickness selected to optimize the evanescent coupling of light from said input waveguide into said waveguide film.

12. Apparatus for performing evanescent immunofluorescence assays including:
- a composite waveguide comprising:
    - a substrate formed of a first optical material of refractive index $n_1$ and having two parallel planar surfaces separated by a thickness and a surrounding edge, said thickness being between about 1 μm and about 10 mm, and
    - a waveguide film deposited directly onto at least a portion of one of said two parallel planar surfaces and formed of a second optical material having a refractive index $n_2$ which is greater than $n_1$ and a thickness which is between about 0.1 μm and about 10 μm, said waveguide film having a plurality of specific binding molecules immobilized thereto;
- a light source operably disposed to aim a light beam into said composite waveguide for propagation by total internal reflection in said composite waveguide;
- light coupling means operably associated with said composite waveguide for facilitating coupling of light beam thereinto;
- light collection means positioned for collecting light that impinges on a plane spaced from said two parallel planar surfaces; and
- a detector operably disposed with respect to said light collection means to detect the collected light.

13. The apparatus of claim 12, wherein said first and second optical materials are mutually selected from the group of pairwise combinations consisting of: deposited silicon dioxide/silicon oxynitride; quartz or fused silica/silicon oxynitride; silicon oxynitride of refractive index $n_1$/silicon oxynitride of refractive index $n_2$; and magnesium fluoride/deposited silicon dioxide.

14. The apparatus of claim 12, wherein said light coupling means is a waveguide coupler contactingly disposed on said waveguide film, and comprising:
- an input waveguide formed of an optical material having a refractive index $n_3$, and having a thickness which is between about 0.5 mm and about 5 mm; and
- a spacing layer formed of an optical material having a refractive index $n_4$, wherein $n_4<n_2$ and $n_4<n_3$, and having a thickness selected to optimize the evanescent coupling of light from said input waveguide into said waveguide film.

15. The apparatus of claim 13, wherein said waveguide film is constructed to have propagation losses in air of less than about 1 dB/cm.

16. An optical structure for performing specific binding assays with an optical unit comprising a light source positioned to direct light into a waveguide for propagation by total internal reflectance in said waveguide and a detector oriented to detect light from a region proximal to the optical structure, said optical structure comprising:
- a substrate comprising a first optical material of refractive index $n_1$ and having two parallel planar surfaces separated by a thickness and a surrounding edge, the thickness being between about 0.3 μm and about 10 mm;
- a waveguide film of a second optical material of refractive index $n_2$, wherein $n_2$ is greater than $n_1$, in direct contact with at least a portion of one of said two parallel planar surfaces of said substrate, said waveguide film having a thickness which is between about 0.3 μm and about 5 μm, and said waveguide film further having a plurality of specific binding molecules immobilized thereto; and
- coupling means for coupling light into said waveguide film, said coupling means integrally contacting said waveguide film.

17. The optical structure of claim 16, wherein said second optical material is selected from the group consisting of: silicon oxynitride of refractive index $n_2$ and silicon dioxide; and said first optical material is selected from the group consisting of: pure silicon dioxide, quartz or fused silica, silicon oxynitride of refractive index $n_1$, and magnesium fluoride.

18. The optical structure of claim 17, wherein said coupling means is selected from the group consisting of: an optical grating formed of said first material; an optical grating formed of said second material; and a waveguide coupler integrally mounted on said waveguide film, said waveguide coupler comprising
- an input waveguide constructed to receive light through an edge and to propagate the received light by total internal reflection, and
- a spacing layer interposed between said input waveguide and said waveguide film and having a thickness selected to optimize the evanescent coupling of light from said input waveguide into said waveguide film.

19. The optical structure of claim 18, wherein said first optical material is quartz, fused silica or deposited $SiO_2$, said coupling means is said waveguide coupler, and wherein said input waveguide is formed of an optical material selected from the group consisting of: rutile, zirconia, and high-index glass; and wherein said spacing layer is formed of silicon dioxide and has a thickness of between about 0.1 μm and about 5 μm.

20. The optical structure of claim 16, wherein said waveguide film is configured as a plurality of strips of said second optical material adhered to one of said two parallel planar surfaces in a spaced parallel array.

21. The optical structure of claim 16, further comprising a plurality of sample wells formed thereon, said sample wells formed by the steps of:
- epitaxially depositing an outer layer of refractive index $n_1$ upon said waveguide film;
- applying a resist compound to a plurality of outlines which define said sample wells while leaving areas within and without the outlines uncoated; and
- removing said outer layer by etching to expose said waveguide film in said uncoated areas.

* * * * *